(12) United States Patent
Poncelet et al.

(10) Patent No.: US 6,361,699 B2
(45) Date of Patent: Mar. 26, 2002

(54) APPARATUS FOR PUTTING INTO CONTACT A DEFINED QUANTITY OF A TREATMENT MATERIAL WITH AN AQUEOUS SOLUTION TO BE TREATED AND PROCESS FOR TREATING AN AQUEOUS SOLUTION

(75) Inventors: Olivier Poncelet, Chalon sur Saone; Danielle Marie Wettling, Chatenoy le Royal, both of (FR)

(73) Assignee: Eastman Kodak Company, Rochester, NY (US)

( * ) Notice: Subject to any disclaimer, the term of this patent is extended or adjusted under 35 U.S.C. 154(b) by 0 days.

(21) Appl. No.: 09/812,646

(22) Filed: Mar. 20, 2001

(30) Foreign Application Priority Data

Mar. 31, 2000 (FR) .............................. 00 04253

(51) Int. Cl.[7] .................................. C02F 1/50
(52) U.S. Cl. ..................... 210/764; 210/198.1; 210/205
(58) Field of Search .............................. 210/764, 198.1, 210/205

(56) References Cited

U.S. PATENT DOCUMENTS

| 3,431,569 | A | * | 3/1969 | Gerke |
| 3,754,871 | A | * | 8/1973 | Hessel et al. |
| 4,040,515 | A | * | 8/1977 | Hessel et al. |
| 4,687,577 | A | * | 8/1987 | Reuter et al. |
| 5,076,465 | A | | 12/1991 | Lawson |
| 6,117,315 | A | * | 9/2000 | Masson |

FOREIGN PATENT DOCUMENTS

| EP | 0 937 393 | 8/1999 |
| WO | 93 10739 | 6/1993 |

* cited by examiner

Primary Examiner—Betsey Morrison Hoey
(74) Attorney, Agent, or Firm—David A. Novais

(57) ABSTRACT

The present invention relates to an apparatus for putting into contact a defined quantity of treatment material with an aqueous solution to be treated. The apparatus comprises at least one medium permeable to the aqueous solution to be treated in which the treatment material is placed. The medium is made of polyester foam and has the form of a closed envelope. The treatment material present in the at least one medium is a material for trapping a compound to be eliminated from the solution.

9 Claims, 2 Drawing Sheets

APPARATUS FOR PUTTING INTO CONTACT A DEFINED QUANTITY OF A TREATMENT MATERIAL WITH AN AQUEOUS SOLUTION TO BE TREATED AND PROCESS FOR TREATING AN AQUEOUS SOLUTION

FIELD OF THE INVENTION

The present invention relates to an apparatus for putting into contact a defined quantity of treatment material with an aqueous solution to be treated, and in particular an apparatus for putting a biocide material into contact with an aqueous solution liable to develop microorganisms. The invention also relates to a treatment process of the aqueous solution liable to develop microorganisms. The apparatus can also be used in particular to put into contact a material capable of trapping silver with a photographic processing solution.

BACKGROUND OF THE INVENTION

In the industrial field, the growth of microorganisms in aqueous solutions is a known phenomenon that requires the utilization of biocide. The role of biocides is to inhibit the growth and/or proliferation of microorganisms. In particular in the field of photography it is known that when the growth of microorganisms is not checked, the aqueous solution transforms into slurry that causes the clogging-up of equipment, the deterioration of processing baths and a deterioration of the quality of the photographic images.

For environmental protection reasons it is desirable to reduce the quantity of biocide necessary for the inhibition of the growth of microorganisms. In fact too much biocide in effluents is not acceptable when these effluents have to be treated by a purification plant.

The French patent application No. 9915123 describes a biocide material that enables the quantities of biocides necessary to inhibit microorganism growth to be reduced and that stays active for several weeks.

It is a material comprising a water permeable matrix in which a mixture of biocides is dispersed of which at least one of the biocides is a hydrophilic biocide and at least one of the biocides is a hydrophobic biocide, the biocide materials being chosen from among the isothiazolones. To be active the biocide material must be crossed by the aqueous solution to be treated, for example water. Such material is utilized in gel form.

To be utilizable the biocide material in gel form and more generally all treatment material must be confined in a container to prevent unwanted diffusion in the solution to be treated.

SUMMARY OF THE INVENTION

It is an object of the invention to provide an apparatus for putting into contact a controlled quantity of treatment material with an aqueous solution which is easy to set up.

It is another object of the invention to provide an apparatus for putting into contact a controlled quantity of treatment material with an aqueous solution that enables the treatment material to be correctly confined while maximizing its efficiency.

It is yet another object of the invention to provide a treatment process for an aqueous solution implemented by an apparatus that is easy to set up and which enables the treatment material to be correctly confined while maximizing its efficiency.

The invention relates to an apparatus for putting into contact a defined quantity of treatment material with an aqueous solution to be treated. The apparatus comprises at least one medium permeable to the aqueous solution in which the treatment material is placed. The medium is made of polyester foam and has the form of a closed envelope. The treatment material present in the at least one medium is a material for trapping a compound to be eliminated from the solution.

The invention also relates to a process for treating an aqueous solution comprising the step of putting into contact the aqueous solution with a treatment material in the apparatus for putting into contact a defined quantity of treatment material.

BRIEF DESCRIPTION OF THE DRAWINGS

Other characteristics will appear on reading the following description, with reference to the drawings wherein.

DETAILED DESCRIPTION OF THE INVENTION

Figure 1:
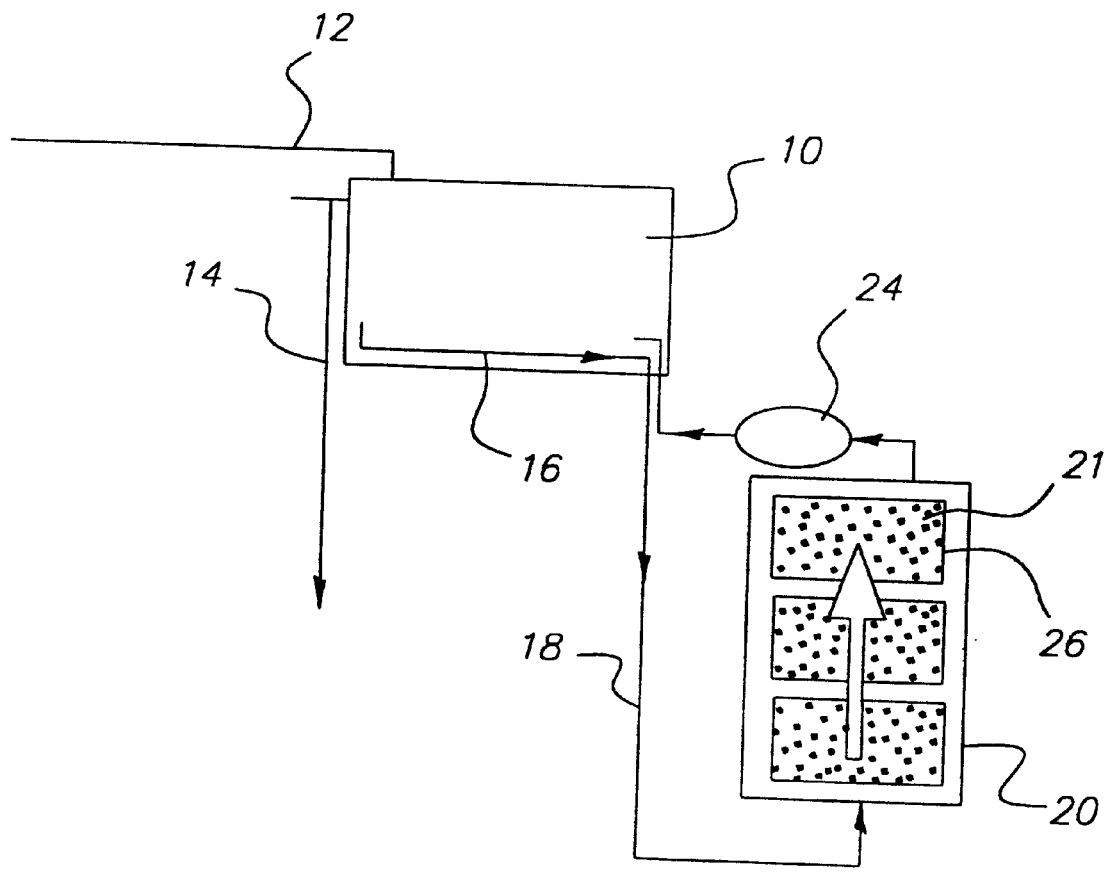
FIG. 1 shows a general schematic diagram of the apparatus according to the invention in a particular installation.

Referring now to FIG. 1, one embodiment of the apparatus according to the invention in a particular installation is shown. A tank 10 contains an aqueous solution liable to develop microorganisms. The tank 10 is water fed through a duct 12. This tank 10 is fitted with an overflow 14 that enables the volume of solution in the tank 10 to be kept constant. In addition the tank 10 is fitted with an outlet 16 connected by a duct 18 to an apparatus 20 for putting a controlled quantity of treatment material, in this case a biocide material, in contact with the aqueous solution to be treated. The apparatus 20 comprises at least one treatment unit 26, for example a tray. The apparatus 20 is connected to a pump 24 that enables the treated solution to be sent back into the tank 10 according to a defined flow rate. The apparatus 20 according to the invention comprises, in each treatment unit 26, at least one medium 21 permeable to the aqueous solution to be treated in which is confined the biocide material. The medium 21 is simply put into the treatment unit 26.

The apparatus for putting the biocide into contact with the aqueous solution is preferably arranged as described above and shown in FIG. 1. However, it is possible to insert it directly into the tank containing the solution to be treated. In this case, the solution could be made to circulate inside the tank itself through the biocide material.

Figure 2:
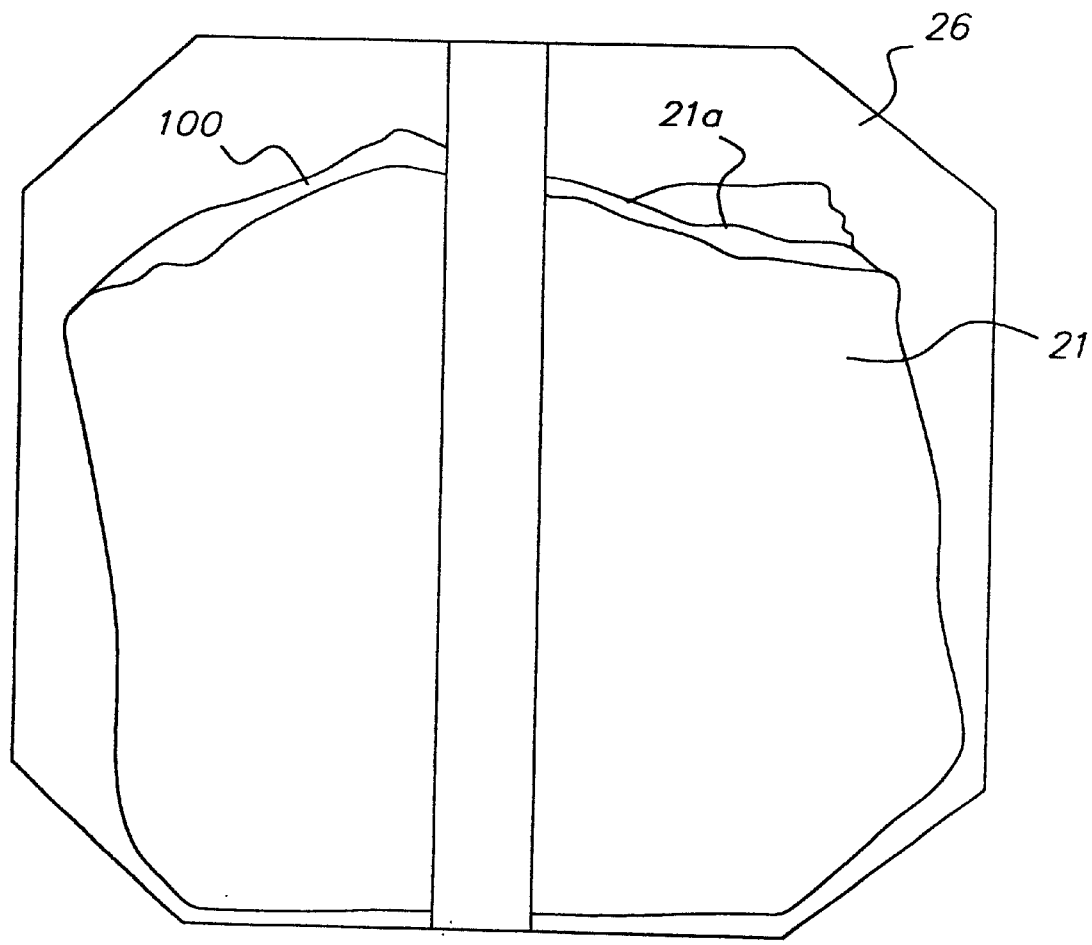
FIG. 2 shows one embodiment of the medium of the treatment material.

FIG. 2 shows one embodiment of the medium 21 containing the biocide. According to the invention, the medium 21 has the form of a closed envelope. In certain cases the biocide material may be prepared directly in the medium 21. However, it may be prepared separately and inserted into the medium 21. To make filling easy, it is desirable that the medium 21 is in the form of an envelope having an opening 100 through which the biocide material can be inserted. Advantageously, the envelope has a self-fastening part 21a to enable easy closing of the envelope after filling. The self-fastening part is for instance Velcro® type. The form of the closed envelope has the advantage of correctly confining the biocide material. However, the solution to be treated must be able to pass through the medium 21 so as to activate the biocide material. Thus the material utilized to produce the medium 21 must be sufficiently porous to let the solution pass and prevent the biocide material that is, as was seen above, present in gel form, from escaping freely from the medium. To this end, the medium 21 according to the invention is made from polyester foam.

According to one embodiment of the invention apparatus, treatment unit or tray 26 is used in which is placed envelope 21, for example 22 cm long by 22 cm wide. The polyester foam utilized to make the envelope is for example made of heat bonded polyester fibers. It has for example thickness 14 mm.

The envelope according to the invention has many advantages. Indeed it can be reopened so that, for example, a small quantity of biocide material present inside can be sampled in order for example to analyze the material. Thus, during utilization, the user can easily check that the biocide material is still sufficiently active and then re-close the envelope thanks to the self-fastening part to continue normal utilization. Similarly, the user can open the envelope and empty it of its contents if necessary and then clean it in order to refill it again. Indeed the polyester foam can be regenerated unlike other materials like, for example, woven material. The user can also wash the envelope in case of clogging-up.

The medium 21 of the invention also has the advantage of not suffering load losses during utilization.

Advantageously, the medium 21 in polyester foam has a filter function and enables the apparatus assembly to be kept clean, that is the treatment tank and the apparatus for delivering the biocide, for a long period of time. In fact it enables various impurities coming from the tank to be filtered mechanically.

The solution to be treated liable to contain bacteria is put into contact with the biocide material by crossing the apparatus 20 that contains at least one medium 21 in which the biocide material is found. By crossing this biocide material, the solution is loaded with biocide. This solution loaded in biocide is then sent back to the treatment tank 10. It is thus possible to limit bacteriological growth in the solution.

The apparatus for putting a defined quantity of treatment material into contact in an aqueous solution to be treated can be utilized in any application in which the water quality in bacteriological terms has to be controlled. For example, the apparatus can be utilized in the photographic sector, the maintenance of industrial cooling waters, etc.

The invention apparatus can be utilized advantageously in a photographic processing machine. In particular, it is especially advantageous to utilize it in the field of conventional medical imaging, a field where it is desirable to have the maximum reduction of bacteriological proliferation. Indeed, in X-ray film processing processes, the presence of bacteria causes defects on the developed films. Such defects can falsify the diagnosis. Moreover, bacterial proliferation causes the formation of a biofilm on the walls of the treatment tanks and on the cylinders and rollers guiding the film, which requires machines to be stopped for cleaning.

Processing machines conventionally comprise a developing bath, a bleaching bath, a fixing bath and one or more wash baths. The invention apparatus can be utilized on any of these baths, preferably to treat a wash bath. The apparatus utilized in this application may comprise several treatment units 26 each one comprising a medium filled with biocide material. In the particular embodiment of FIG. 1, the apparatus 20 for delivering the biocide material has three treatment units 26 of which at least one unit contains the medium 21 filled with biocide material. In this application the medium 21 is also utilized to put into contact a treatment material of a different nature, for example a material for trapping compounds to be eliminated from the solution. For example, the other units may contain a material capable of trapping the silver contained in the solution to be treated. The treatment material present in the medium 21 is then constituted of imogolite whose surface has been altered and which includes thiol groups able to collect the silver ions present in the solution to be treated.

The invention apparatus can also be used in the field of motion picture processing for preventing the formation of precipitates in the processors, and/or for decreasing the frequency of their cleaning. Due to the configuration and the volume of the baths to treat, the apparatus comprises a plurality of media 21 which are attached together. Such a design permits the optimization of the interaction between the media and the fluid to be treated. It also limits the elastic deformation due to gravity which is particularly advantageous since the apparatus is used during a long period of time.

The invention has been described in detail with particular reference to certain preferred embodiments thereof, but it will be understood that variations and modifications can be effected within the spirit and scope of the invention.

What is claimed is:

1. An apparatus for putting into contact a defined quantity of treatment material with an aqueous solution to be treated without suffering load losses, the apparatus comprising:
   at least a first treatment unit wherein a first medium having a filter function and being permeable to the aqueous solution is placed into the first treatment unit, the first medium being made of polyester foam and having a form of a closed envelope which can be reopened, and wherein a first treatment material is placed in said first medium for treating aqueous solution which is liable to develop microorganisms;
   a least a second treatment unit wherein a second medium having a filter function and being permeable to the aqueous solution is placed into the second treatment unit, the second medium being made of polyester foam and having a form of a closed envelope which can be reopened, and wherein a second treatment material is placed in said second medium for trapping a compound to be eliminated from the solution.

2. The apparatus of claim 1, wherein the first treatment material present on the first medium is a biocide material provided to prevent the development of microorganisms liable to be developed in the aqueous solution to be treated, and wherein the second treatment material present in the second medium is an imogolite whose surface has been altered, the imogolite including thiol groups which are capable of collecting silver ions present in the aqueous solution to be treated.

3. The apparatus of claim 1, wherein the envelopes of the first medium and the second medium comprises a self-fastening part enabling its closure.

4. The apparatus of claim 3, wherein the self-fastening part is Velcro® type.

5. The apparatus of claim 1, wherein the biocide present in the first medium is in gel form.

6. The apparatus of claim 1, wherein the apparatus is connected to a tank which contains the aqueous solution to be treated so as to make the aqueous solution circulate according to a defined flow rate in the apparatus.

7. A process for treating an aqueous solution without suffering load losses comprising:
   putting into contact the aqueous solution with two different treatment material in an apparatus comprising at least first and second media permeable to the aqueous solution, the two treatment materials being respectively confined in said first and second media, and wherein the first and second media are made of polyester foam and have the form of a closed envelope which can be reopened.

8. The process of claim 7 for treating photographic baths.

9. The process of claim 8 for treating a photographic wash bath.

* * * * *